US00PP13549P2

(12) United States Plant Patent
Heims

(10) Patent No.: US PP13,549 P2
(45) Date of Patent: Feb. 4, 2003

(54) PENSTEMON PLANT NAMED 'SWEET GRAPES'

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 09/989,927

(22) Filed: Nov. 20, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—Klarquist Sparkman, LLP

(57) ABSTRACT

A new and distinct hybrid of Penstemon plant characterized by purple flowers on short, strong inflorescences and a compact, suffrutescent habit.

1 Drawing Sheet

Botanical name: Penstemon hybrid.
Cultivar name: 'Sweet Grape'.

BACKGROUND OF THE INVENTION

The present invention relates to a new and distinct cultivar of a suffrutescent perennial, Penstemon hybrid, of the family Scrophulariaceae, which originated as a seedling selection from the Saskatoon Hybrids. The Saskatoon Hybrids are a hybrid seed strain involving *Penstemon barbatus, P. glaber, P. clutei, P. palmeri,* and others.

SUMMARY OF THE INVENTION

This new cultivar is characterized by:

1. Deep purple flowers.
2. High flower number on a tight inflorescence.
3. Persistent basal foliage with a compact habit.
4. More tolerant to winter wet soil conditions than most Penstemon.

This new cultivar has been reproduced only by asexual propagation (division and tissue culture). Each of the progeny exhibits identical characteristics to the original plant. Asexual propagation by tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions, The phenotype may vary with variations in environment without a change in the genotype of the plant.

BRIEF DESCRIPTION OF THE DRAWING

The drawing shows a one-year-old Penstemon 'Sweet Grapes' growing in the garden in Canby, Oreg.

DETAILED PLANT DESCRIPTION

The following is a detailed description of the new Penstemon hybrid based on observations of three-year-old specimens grown in the garden Canby, Oreg. The color descriptions are all based on The Royal Horicultural Society Colour Chart.

Plant:
- *Type*.—Herbaceous perennial.
- *Form*.—Compact basal rosette.
- *Hardiness*.—USDA Zone 4 to 9.
- *Size*.—13 cm tall and 48 cm wide, not including bloom.
- *Habit*.—Suffrutescent, foliage doesn't die down in the winter.

Leaf:
- *Type*.—Simple.
- *Arrangement*.—Opposite.
- *Shape*.—Lanceolate.
- *Venation*.—Pinnate.
- *Margins*.—Entire, sometimes somewhat undulate.
- *Apex*.—Acuminate.
- *Base*.—Sessile, obtuse.
- *Blade size*.—9 to 12 cm long and 1.4 to 1.8 cm wide.
- *Vestiture*.—Glabrous.
- *Aspect*.—Glossy.
- *Texture*.—Leathery.
- *Leaf color*.—Deep green. Between Yellow Green 147A and Green 137A top and bottom, with prominent main vein on bottom, Yellow Green 145B.

Inflorescence:
- *Type*.—Thryse.
- *Number of flowers*.—50 to 75 per thryse.
- *Peduncle*.—Height — 32 cm. Diameter — 0.6 cm. Color — Yellow Green 145B. Texture — Glabrous.
- *Pedicel*.—Length — 1 to 1.5 cm. Texture — Glabrous. Color — Yellow Green 145B.
- *Bloom period*.—June to July.

Flower bud:
- *Size*.—3 cm. long and 0.8 cm wide.
- *Description*.—Closed tubular, bulging.
- *Color*.—Purple 77A.

Flower:
- *Type*.—Perfect, zygomorphic.
- *Shape*.—Tubular, bilabiate. With a narrow tube for 0.5 cm, inflating for 1.7 cm, flaring into the lobes. Two top lobes shallowly cut and three bottom more deeply divided, flare down, and curl back at the sides.
- *Size*.—3.5 cm long and 1.7 cm wide at flare.
- *Color*.—Purple 77A on upper lobes and tube with White 155D in a band at the base of the lower lobes and Purple 77B on lower lobes.

*Calyx*.—5 lobes, cut ⅔ to base, overlapping, ovate shaped lobes, margins irregularly serrate, acuminate tip. Campanulate.

*Calyx size*.—0.5 cm deep and 0.35 cm wide.

*Calyx color*.—Yellow Green 145A.

*Stamen number*.—5, one sterile, held within the corolla.

*Stamen shape*.—Parallel, dehiscent across the connective, bearded on backsides.

*Filaments*.—2.5 cm long. Light Purple 76C near base to White 155A near anthers.

*Anther size*.—2.5 mm.

*Pollen color*.—Yellow White 158B.

*Pistil*.—2.8 cm long, Yellow White 158D.

*Fragrance*.—None.

*Lastingness*.—Each cyme blooms for about 3 weeks on the plant. Removal of spent cymes will induce secondary and tertiary bloom periods. This greatly extends the bloom period.

Fruit:

*Type*.—Capsule.

*Fertility*.—Good.

*Size*.—1.2 cm deep and 0.4 cm wide.

*Color*.—Brown 200A to B.

Seed:

*Shape*.—Irregular.

*Size*.—2 mm. long.

*Color*.—Brown 200A.

Disease tolerance: Excellent disease tolerance to root rots, a common problem for Penstemon.

Comparisons to Similar Penstemon

The problems with the seed strain, Penstemon Saskatoon Hybrids, are:

1. Many don't bloom the first year or have poor quality bloom;
2. They vary in plant size from 20 cm. to 1 m.;
3. Many have floppy inflorescences;
4. Many have open centers.

Compared to Penstemon Saskatoon Hybrids, a Penstemon 'Sweet Grapes' blooms in the first year; has flowers with good size and good purple color; inflorescences that are short with good flower number; and a neat, compact habit.

Compared to Penstemon 'Pink Chablis' (U.S. Plant patent application Ser. No. 09/989,946), Penstemon 'Sweet Grapes' has purple flowers rather than deep pink.

I claim:

1. A new and distinct hybrid of Penstemon plant substantially as shown and described, characterized by purple flowers on short, strong inflorescences, and a compact, suffrutescent habit.

* * * * *

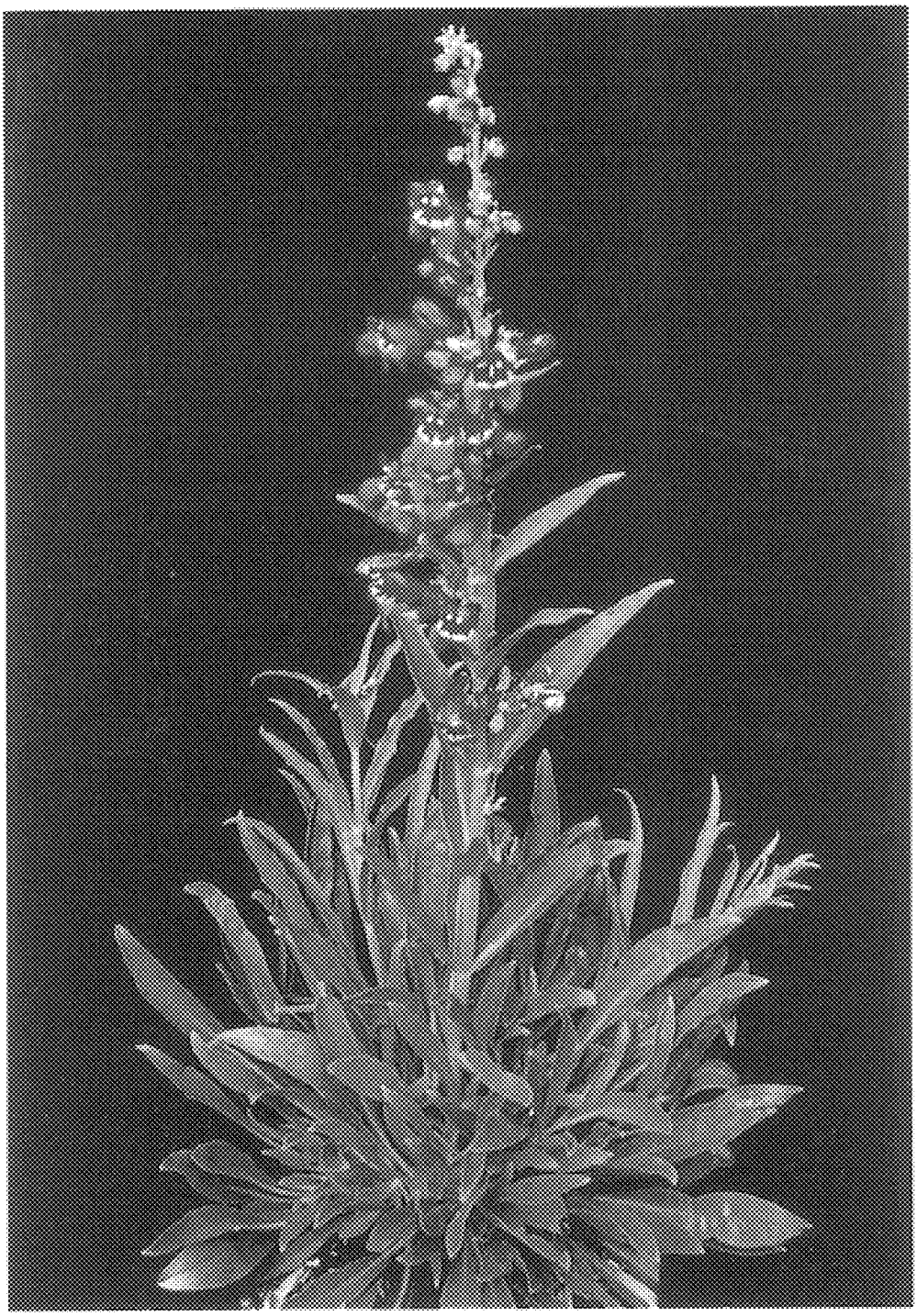

UNITED STATES PATENT AND TRADEMARK OFFICE

CERTIFICATE OF CORRECTION

PATENT NO. : PP 13,549 P2
APPLICATION NO. : 09/989927
DATED : February 4, 2003
INVENTOR(S) : Daniel M. Heims It is certified that error appears in the above-identified patent and that said Letters Patent is hereby corrected as shown below:

In column 1, line 2, the cultivar name reads “Sweet Grape”. The cultivar name should be --Sweet Grapes--.

Signed and Sealed this

Fifteenth Day of August, 2006

JON W. DUDAS
*Director of the United States Patent and Trademark Office*